(12) United States Patent
Oh et al.

(10) Patent No.: US 8,198,325 B2
(45) Date of Patent: Jun. 12, 2012

(54) UNSATURATED ALKYL ESTERS OF 5-AMINOLEVULINIC ACID, THEIR PREPARATION AND THEIR USE

(75) Inventors: Jonghoon Oh, Gwangju (KR); Jee-Bum Lee, Gwangju (KR); Hyoung-Ryun Park, Gwangju (KR)

(73) Assignee: Industry Foundation of Chonnam National University, Gwangju (KR)

( * ) Notice: Subject to any disclaimer, the term of this patent is extended or adjusted under 35 U.S.C. 154(b) by 666 days.

(21) Appl. No.: 12/227,085

(22) PCT Filed: Jun. 28, 2007

(86) PCT No.: PCT/KR2007/003145
§ 371 (c)(1),
(2), (4) Date: Dec. 4, 2008

(87) PCT Pub. No.: WO2008/002087
PCT Pub. Date: Jan. 3, 2008

(65) Prior Publication Data
US 2009/0176881 A1    Jul. 9, 2009

(30) Foreign Application Priority Data

Jun. 29, 2006  (KR) .................. 10-2006-0059124
Apr. 26, 2007  (KR) .................. 10-2007-0040869

(51) Int. Cl.
*A61K 31/22*   (2006.01)
*C07C 229/00*  (2006.01)

(52) U.S. Cl. ........................ 514/551; 560/170
(58) Field of Classification Search .............. None
See application file for complete search history.

(56) References Cited

U.S. PATENT DOCUMENTS 6,034,267 A * 3/2000 Gierskcky et al. ............ 560/155
2009/0118509 A1 * 5/2009 Arora et al. .................. 544/364

FOREIGN PATENT DOCUMENTS

WO  WO 96/28412       9/1996
WO  WO 2005/092838 A1 6/2005
WO  WO 2006/051269 A1 5/2006

OTHER PUBLICATIONS

Jo et al, Bulletin of the Korean Chemical Society, Synthesis and Evaluation of Unsaturated Alkyl Esters of 5-Aminolevulinic Acid as Precursors to Photoporphyrin IX, 2007, 28(1), pp. 129-132.*
STN International, File CAPLUS, Accession No. 2003:362062, Document No. 140:117154, Turchiello, R. F. et al., *Cubic phase gel as a drug delivery system for topical application of 5-ALA, its ester derivatives and m-THPC in photodynamic therapy(PDP)*, Journal of Photochemistry and Photobiology, B: Biology, vol. 70, (2003) pp. 1-6, ISSN: 1011-1344.
International Search Report, dated Oct. 22, 2007, corresponding to PCT/KR2007/003145.
STN International, File Caplus, Accession No. 2003:362062, Document No. 140:117154, Turchiello, R. F. et al., Cubic phase gel as a drug delivery system for topical application of 5-ALA, its ester derivatives and m-THPC in photodynamic therapy(PDP), Journal of photochemistry and Photobiology, B: Biology, 2003, vol. 70, No. 1, pp. 1-6, ISSN: 1011-1344 (On Order).

* cited by examiner

*Primary Examiner* — Paul A Zucker
(74) *Attorney, Agent, or Firm* — Christie, Parker & Hale, LLP

(57) ABSTRACT

Disclosed are unsaturated alkyl esters of 5-aminovulinic acid of the following chemical formula 1, or pharmaceutically acceptable salts thereof, a method for preparing the same, and uses thereof. [Chemical Formula I] $NH_2-CH_2-CO-CH_2-CH_2-CO-O-R$ wherein, R is a group selected from a group consisting of 2-propenyl, 3-butenyl, 4-pentenyl, 5-hexenyl, cis-2-pentenyl, cis-3-hexenyl, cis-4-hexenyl, and trans-2-hexenyl. Also, a pharmaceutical composition comprising the unsaturated alkyl ester of 5-aminovulinic acid or a salt thereof as an active ingredient is provided. This pharmaceutical composition is easily absorbed transdermally and is of low cytotoxicity. Featuring no amino-protecting processes, the method guarantees high production yields.

5 Claims, 11 Drawing Sheets

[Fig. 6]
(A)
(B)
(C)
Control
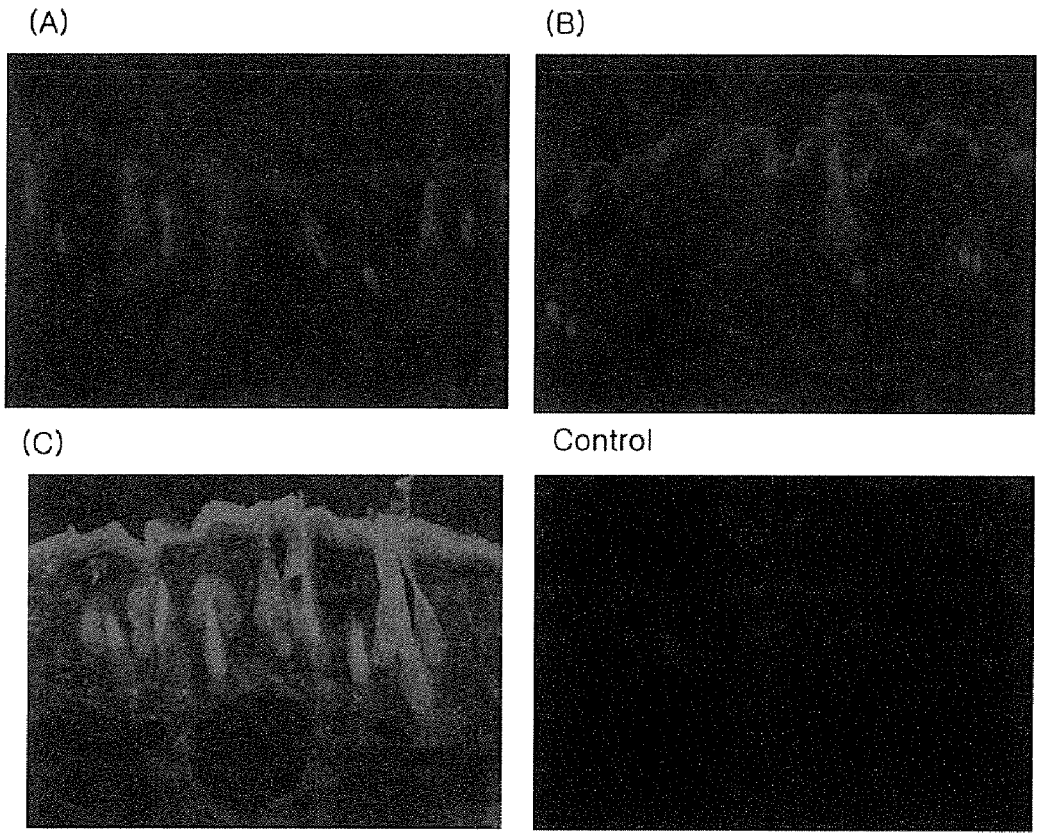
[Fig. 7]
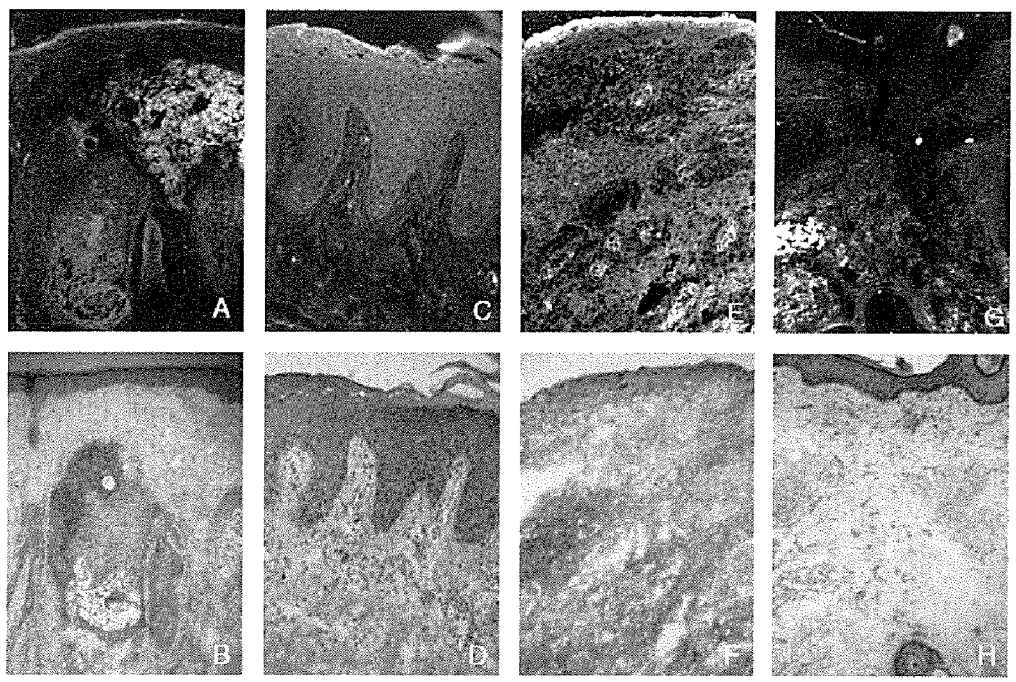

[Fig. 8]
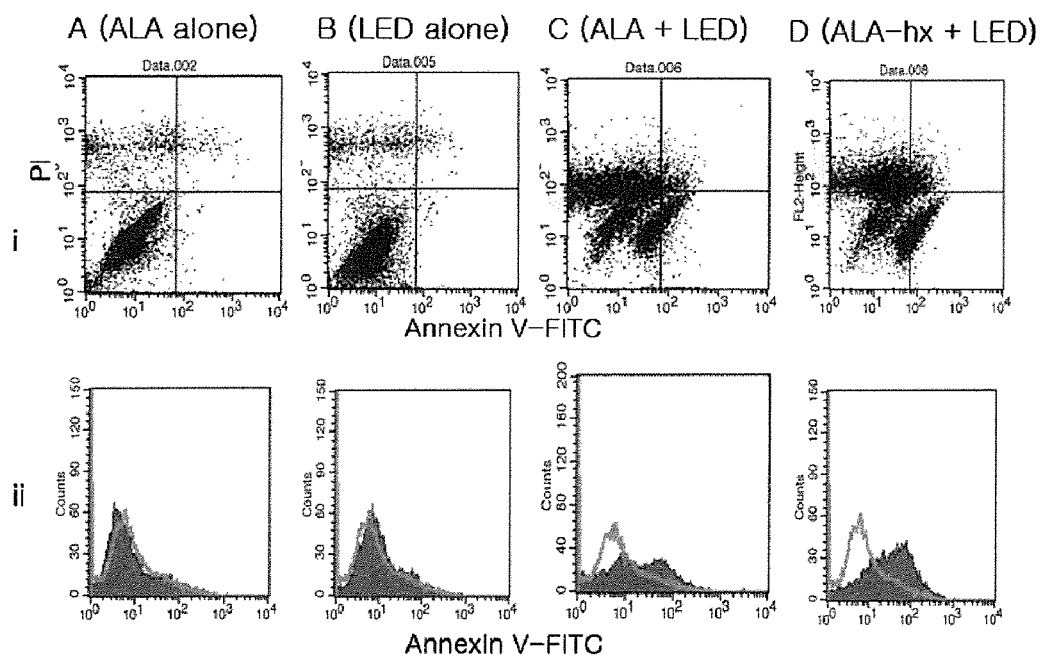
[Fig. 9]
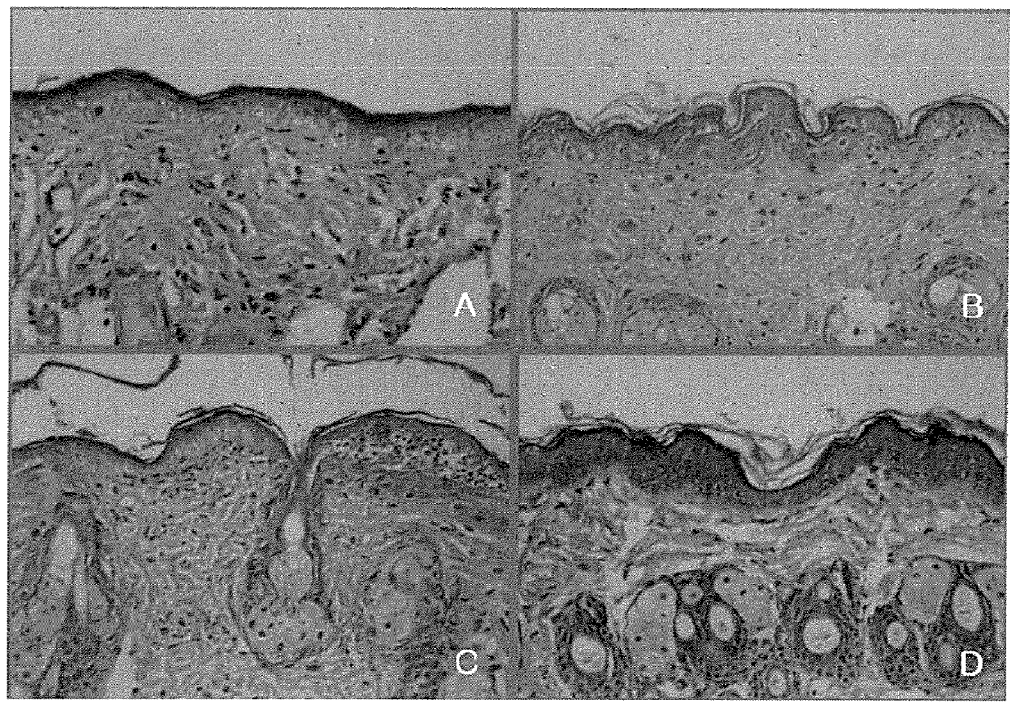

[Fig. 10]
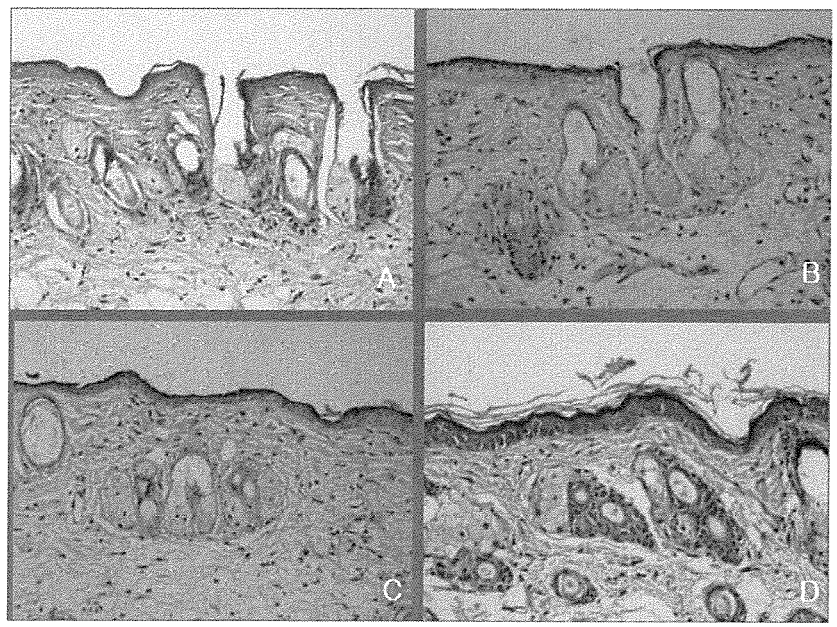
[Fig. 11]
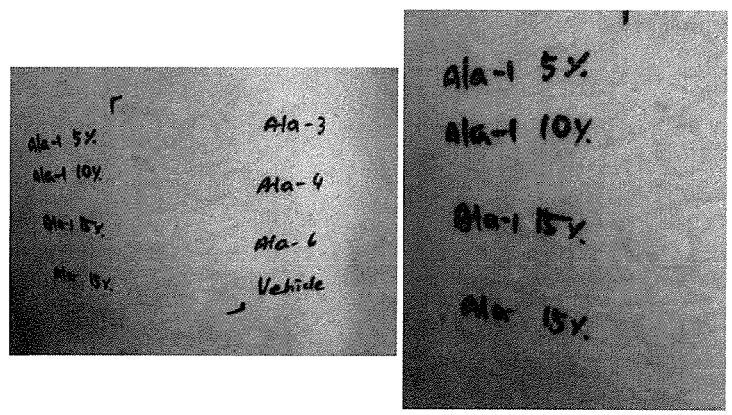
[Fig. 12]
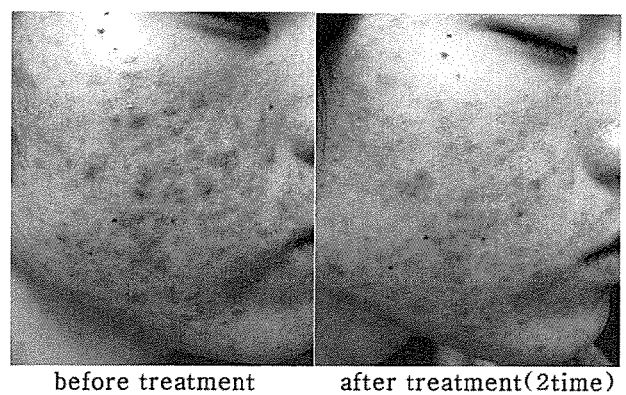
before treatment     after treatment(2time)

[Fig. 13]
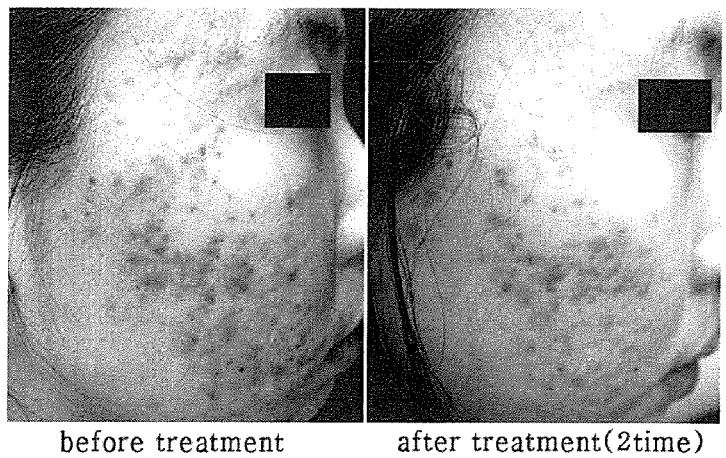
before treatment     after treatment(2time)
[Fig. 14]
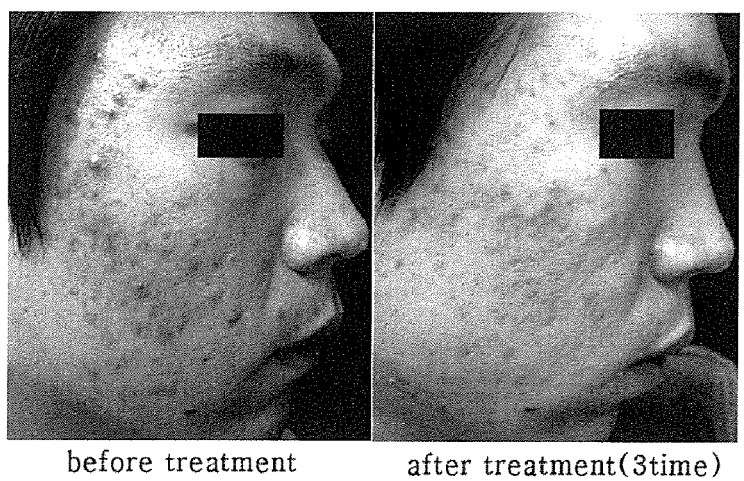
before treatment     after treatment(3time)
[Fig. 15]
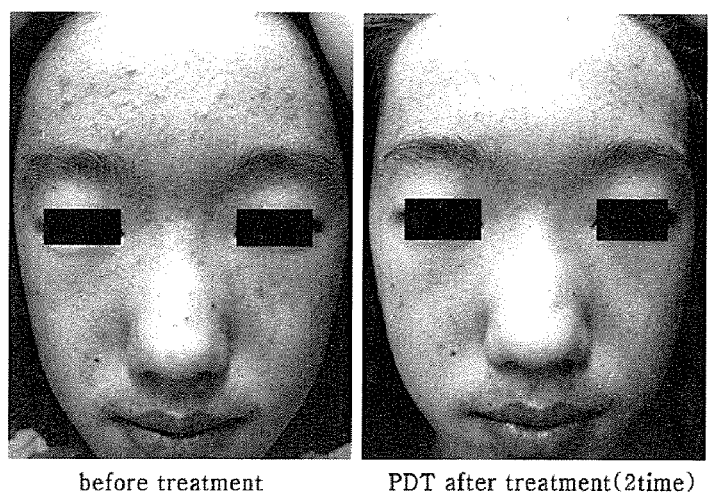
before treatment     PDT after treatment(2time)

[Fig. 16]
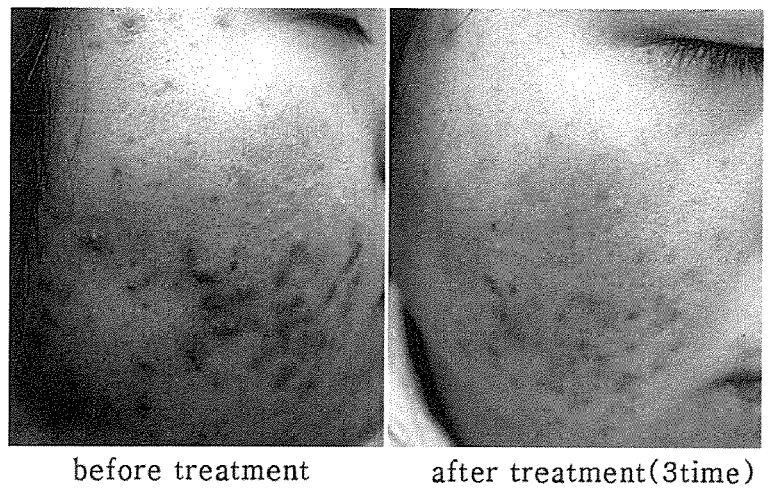
before treatment     after treatment(3time)
[Fig. 17]
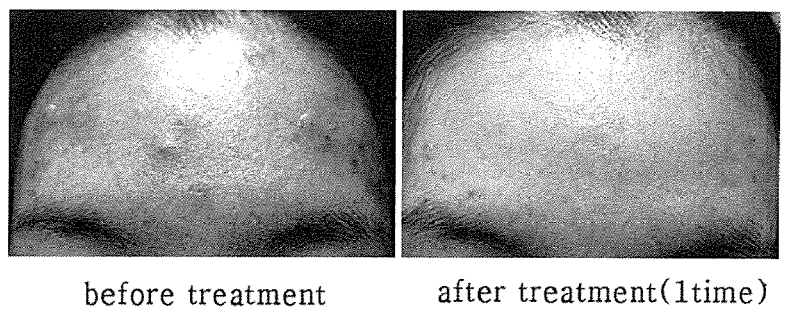
before treatment     after treatment(1time)
[Fig. 18]
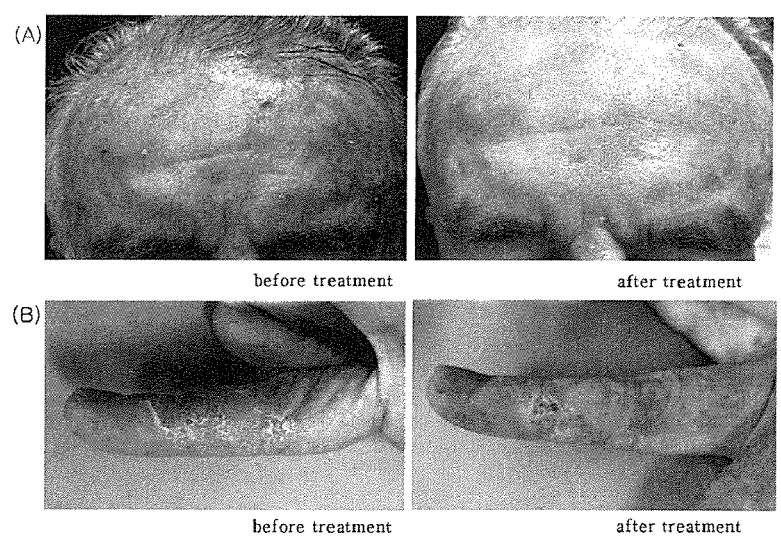

[Fig. 19]
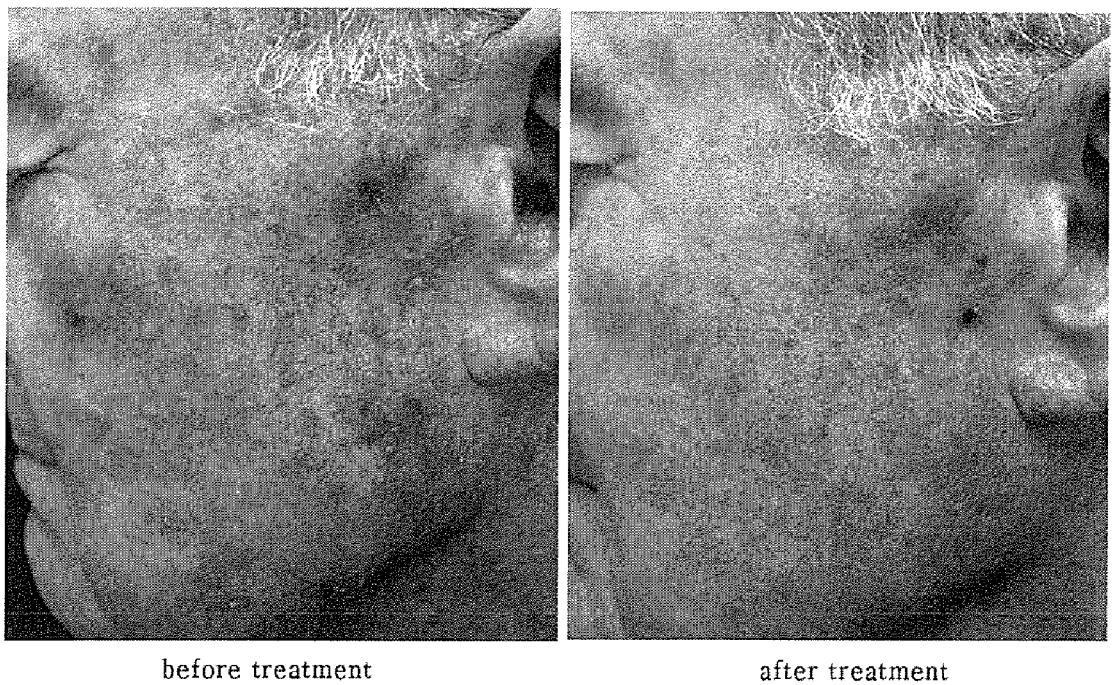
before treatment　　　　　　　　after treatment

UNSATURATED ALKYL ESTERS OF 5-AMINOLEVULINIC ACID, THEIR PREPARATION AND THEIR USE

CROSS-REFERENCE TO RELATED APPLICATION

This application is a National Phase Patent Application of International Application Number PCT/KR2007/003145, filed on Jun. 28, 2007, which claims priority of Korean Patent Application Number 10-2006-0059124, filed on Jun. 29, 2006, and Korean Patent Application Number 10-2007-0040869, filed on Apr. 26, 2007.

TECHNICAL FIELD

The present invention relates to unsaturated alkyl esters of 5-aminolevulinic acid, represented by the following chemical formula 1, pharmaceutically acceptable salts thereof, a method for preparing the same, and uses thereof.

$$NH_2-CH_2-CO-CH_2-CH_2-CO-O-R \quad \text{[Chemical Formula I]}$$

wherein, R is a group selected from a group consisting of 2-propenyl, 3-butenyl, 4-pentenyl, 5-hexenyl, cis-2-pentenyl, cis-3-hexenyl, cis-4-hexenyl, and trans-2-hexenyl.

Also, the present invention is directed to a pharmaceutical composition for the treatment of skin diseases, comprising the compound of Chemical Formula 1 or a pharmaceutically acceptable salt thereof.

BACKGROUND ART 5-aminolevulinic acid (ALA) is an endogenous precursor for photosensitizers formed by heme biosynthesis, and has been studied for photodynamic therapy (PDT) with promising results for some skin diseases.

When absorbed into the skin through topical application, such as coating or patching, ALA migrates into cells and is converted into protoporphyrin IX (PpIX), which is used as an endogenous photosensitizer in photodynamic therapy (PDT).

ALA, under the same conditions, is more rapidly absorbed into abnormal cells or tissues than normal cells or tissues.

PpIX is induced to be fluorescent when exposed to visible light in the frequency range from 450 to 650 nm. Transferring energy to adjacent oxygen molecules, this fluorescence converts them into singlet oxygen, a reactive oxygen species, which functions as a toxin destroying the adjacent cells and tissues thereof.

Therefore, radiation leads to various therapeutic effects on abnormal cells and tissue (skin) in which a high concentration of PpIX is accumulated.

However, the high hydrophilicity and low hydrophobicity thereof prevents ALA from penetrating into such barriers as the stratum corneum and cell membranes. It takes a very long time to accumulate ALA in cells at a sufficient concentration to elicit the desired therapeutic effects.

To address this limitation of uptake and distribution of ALA, the drug has been converted into its esters, such as methyl ester, butyl ester, etc. These alkyl esters are greatly decreased in hydrophilicity compared to carboxylic acid, which makes it easy for them to pass through barriers such as the stratum cornea and cell membranes. However, the compounds find applications only in narrow and limited fields.

Moreover, since the synthesis of the ester derivatives involves a complex process including the introduction of an amino-protecting group and the removal thereof, the production yield becomes too low to apply the process in practice.

Thus, there is a need for a method by which ALA can be effectively carried into cells and which can find application in a variety of fields.

Leading to the present invention, intensive and thorough research into the effective delivery of ALA into cells, conducted by the present inventors, resulted in the finding that unsaturated alkyl esters of ALA can readily penetrate into barriers such as the stratum cornea and cell membranes. Nowhere are such unsaturated alkyl esters of ALA disclosed in the prior art.

Also, a method for synthesizing the esters of ALA at a high yield without using amino-protecting groups was also developed, which can be applied to a variety of fields.

DISCLOSURE

Technical Problem

Accordingly, the present invention has been made keeping in mind the above problems occurring in the prior art, and an object of the present invention is to provide an unsaturated alkyl ester of 5-aminolevulinic acid which can be readily absorbed into cells across the dermal surface, and a pharmaceutically acceptable salt thereof.

It is another object of the present invention to provide a method for preparing the compound at a high yield.

It is another object of the present invention to provide a pharmaceutical composition for the treatment of skin diseases, comprising the compound.

Technical Solution

The advantages, features and techniques to achieve them will be apparent with reference to the following examples. However, the present invention is not limited by the examples to be disclosed below, but may be embodied in various forms. Although the preferred embodiments of the present invention are disclosed for illustrative purposes, those skilled in the art will appreciate that various modifications, additions and substitutions are possible, without departing from the scope and spirit of the invention as disclosed in the accompanying claims. Reference should now be made to the drawings, in which the same reference numerals are used throughout the different drawings to designate the same or similar components.

In accordance with an aspect thereof, the present invention provides an unsaturated alkyl ester of 5-aminolevulinic acid, represented by the following chemical formula I, and pharmaceutically acceptable salts thereof.

$$NH_2-CH_2-CO-CH_2-CH_2-CO-O-R \quad \text{[Chemical Formula I]}$$

wherein, R is a group selected from a group consisting of 2-propenyl, 3-butenyl, 4-pentenyl, 5-hexenyl, cis-2-pentenyl, cis-3-hexenyl, cis-4-hexenyl, and trans-2-hexenyl.

In accordance with another aspect thereof, the present invention provides a method for preparing the unsaturated alkyl ester of 5-aminolevulinic acid, comprising (a) reacting a compound, represented by the following chemical formula II, with thionyl chloride and N,N-dimethylformamide; and (b) reacting a product of step (a) with an unsaturated alcohol selected from a group consisting of allyl alcohol, 3-butenol, 4-pentenol, 5 hexenol, cis-2-pentenol, cis-3-hexenol, cis-4-hexenol and trans-2-hexenol:

$$NH_2-CH_2-CO-CH_2-CH_2-CO-OH \quad \text{[Chemical Formula II]}$$

In accordance with a further aspect thereof, the present invention provides a pharmaceutical composition for the treatment of skin diseases, comprising an unsaturated alkyl ester of 5-aminolevulinic acid or a pharmaceutically acceptable salt thereof as an active ingredient.

The pharmaceutical composition of the present invention is applicable for topical skin diseases, typified by acne and skin cancer. For example, the pharmaceutical composition is useful in the treatment of premalignant skin diseases, such as actinic keratosis or arsenical keratosis, or basal cell cancers.

As described above, the present invention is directed to a compound useful in photodynamic therapy for skin diseases, a pharmaceutical composition comprising the same as an active ingredient, and a method for the preparation thereof. The compound is easily absorbed transdermally and has low cytotoxicity. Involving no amino-protecting processes, the method guarantees high production yields.

The pharmaceutical composition for the treatment of skin diseases in accordance with the present invention may be prepared into topical dosage forms, such as creams, ointments, lotions and patches, by formulating an alkyl ester of 5-aminolevulinic acid or a pharmaceutically acceptable salt thereof with a pharmaceutically acceptable vehicle according to the method described in Remington's Pharmaceutical Sciences Handbook, Mack. Pub. Co., N.Y., USA. Preferably, the pharmaceutical composition of the present invention comprises the alkyl ester of 5-aminolevulinic acid or a pharmaceutically acceptable salt thereof in an amount of about 15% (w/v) or 15% (w/w).

Examples of the vehicle useful in the present invention include a saline, a buffer, dextrose, water, glycerol, Ringer's solution, lactose, sucrose, calcium silicate, methyl cellulose, ethanol, and combinations thereof, but are not limited thereto.

In addition, the pharmaceutical composition for the treatment of skin diseases in accordance with the present invention may comprise a filler, an anti-agglutinant, a lubricant, a wetting agent, a flavor, an emulsifier, and/or a preservative.

The alkyl ester of 5-aminolevulinic acid or the pharmaceutically acceptable salt thereof according to the present invention may be administered in a dose that depends on various factors, including the administration purpose thereof and the severity of the disease to be treated. In greater detail, a single dose of the pharmaceutical composition according to the present invention preferably does not exceed 1 g.

When the pharmaceutical composition of the present invention is uniformly spread or patched over a dermal lesion to be treated, the administration is preferably sustained for (a maximum of) 4 hours.

Since the topical region to which the pharmaceutical composition of the present invention is applied may show a photosensitive response, the application region must be protected from light.

In practice, the site receiving the photodynamic therapy treatment is preferably further coated with a sunscreen for at least 48 hours.

In accordance with the present invention, the compound, which is readily absorbed into cells across the dermal surface and shows low cytotoxicity, can be prepared at a high yield because no amino group-protecting process is involved.

The compounds according to the present invention and the pharmaceutically acceptable salts thereof may be prepared as summarized in the following reaction formulas.

1. 2-propenyl 5-aminolevulinate hydrochloride
   (ALA allyl ester hydrochloride)

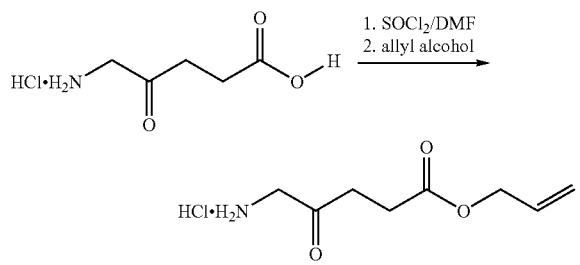

2. 3-butenyl 5-aminolevulinate hydrochloride 3. 4-pentenyl 5-aminolevulinate hydrochloride 4. 5-hexenyl 5-aminolevulinate hydrochloride 5. cis-2-pentenyl 5-aminolevulinate hydrochloride 6. cis-3-hexenyl 5-aminolevulinate hydrochloride 7. cis-4-hexenyl 5-aminolevulinate hydrochloride

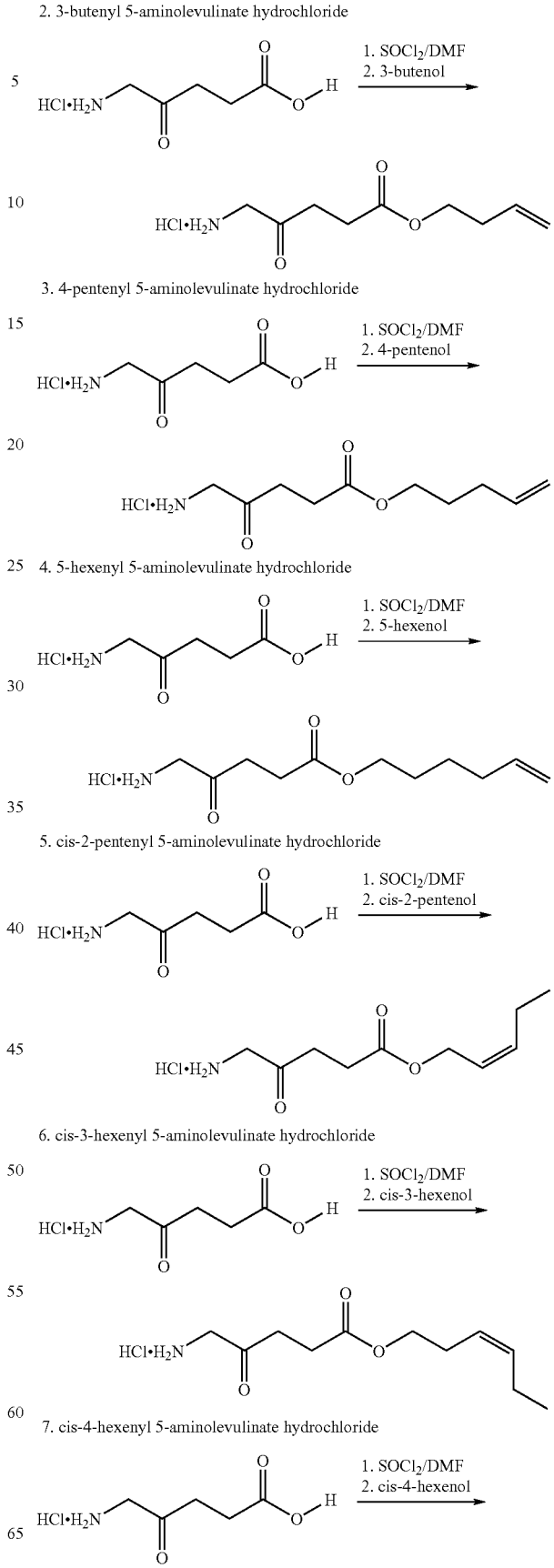

-continued

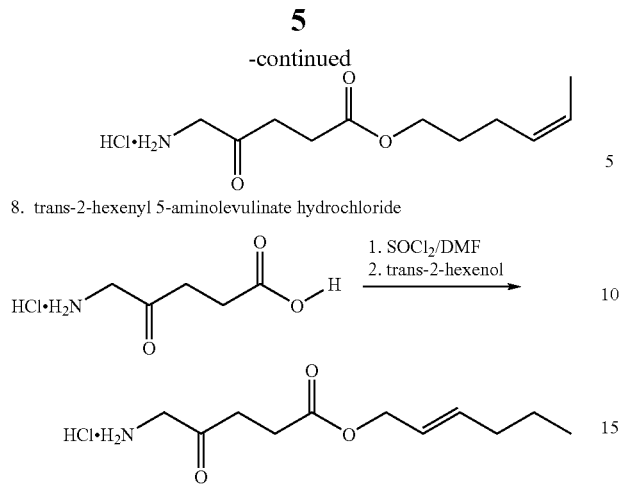

8. trans-2-hexenyl 5-aminolevulinate hydrochloride

Advantageous Effects

The ALA esters according to the present invention have low cytotoxicity and can be readily absorbed across the barrier of the skin into cells.

DESCRIPTION OF DRAWINGS

FIG. 6 shows the fluorescence of PpIX synthesized in the skin of ICR mice 1 hour (A), 2 hours (B) and 3 hours (C) after treatment with the ALA ester of the present invention, FIG. 7 shows PpIX accumulated in lesions of acne (A, B), psoriasis (C, D), "Extramammary Paget's disease" (E, F), and basal cell cancer (G, H) after treatment with ALA and the ALA ester of the present invention in microphotographs (A, C, E and G) and in a histochemical staining manner (B, D, F and H).

FIG. 8 provides FACS (flow cytometry) histograms showing the photo-induced cell death of the Annexin V-stained cells after treatment with ALA and the ALA ester of the present invention.

FIG. 9 shows the necrosis and regeneration of the epidermis of the ICR mice irradiated with visible light after treatment with ALA and the ALA ester of the present invention.

FIG. 10 shows the morphological change in hair follicle and sebaceous gland of the ICR mice treated with ALA and the ALA ester of the present invention according to the time of light irradiation.

FIG. 11 shows the safety of the ALA ester of the present invention as a result of a patch test.

FIGS. 12 to 17 show therapeutic effects of the ointment of the present invention on acne.

FIG. 18 shows the therapeutic effect of the ointment of the present invention on actinic keratosis (A) and arsenical keratosis (B).

FIG. 19 shows the therapeutic effect of the ointment of the present invention on basal cell cancer.

BEST MODE

EXAMPLE

Example 1

Figure 1:
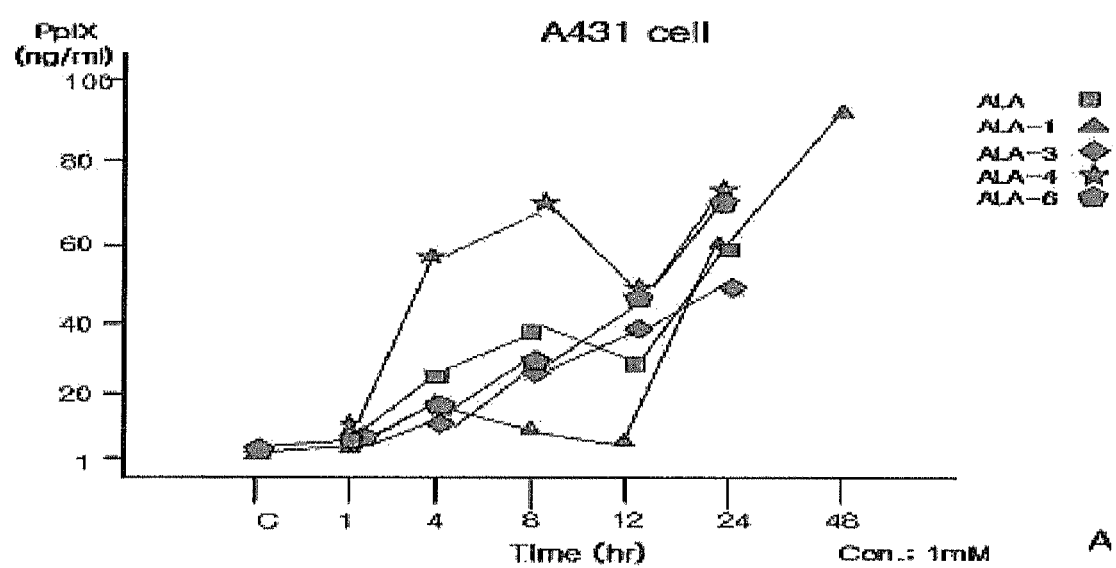
FIG. 1 is a graph showing the amounts of PpIX synthesized in A431 cells treated with the ALA esters of the present invention.

Preparation of 2-Propenyl 5-Aminolevulinate Hydrochloride (ALA Allyl Ester Hydrochloride

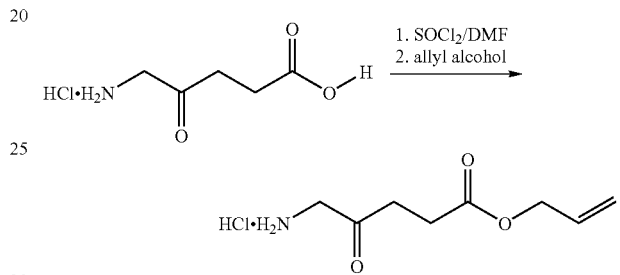

To 1 ml of thionyl chloride ($SOCl_2$) were added 3 drops of N,N-dimethylformamide (DMF) with stirring. Following the addition of 5-aminolevulinic acid hydrochloride (ALA.HCl, 200 mg, 1.19 mmol), the solution was stirred for 12 hours at room temperature. Concentration in a vacuum was conducted before the addition of allyl alcohol. Then, the reaction mixture was stirred for 1.5 hours at room temperature, followed by purification by silica gel chromatography to afford 2-propenyl 5-aminolevulinate hydrochloride, (ALA allyl ester hydrochloride) at a yield of 73%.

$^1$H NMR (300 MHz, DMSO-$d_6$): δ8.57 (s, 3H), 6.2~6.09 (m, 1H), 5.57~5.41 (m, 2H), 4.77 (dt, J=5.4 Hz, 1.5 Hz, 2H), 4.15 (br s, 2H), 3.05 (t, J=6 Hz, 2H), 2.81 (t, J=6 Hz, 2H); $^{13}$C NMR (75 MHz, DMSO-$d_6$): δ171.8, 152.63, 143.22, 132.62, 117.58, 64.36, 31.78, 28.86

Example 2

Preparation of 3-Butenyl 5-Aminolevulinate Hydrochloride

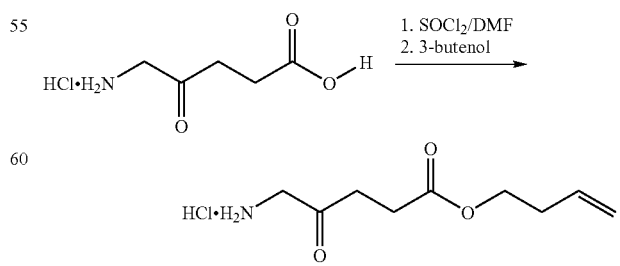

To 1 ml of thionyl chloride ($SOCl_2$) were added 3 drops of N,N-dimethylformamide (DMF) with stirring. Following the addition of 5-aminolevulinic acid hydrochloride (ALA.HCl, 200 mg, 1.19 mmol), the solution was stirred for 12 hours at room temperature. Concentration in a vacuum was conducted before the addition of 3-butenol. Then, the reaction mixture was stirred for 1.5 hours at room temperature, followed by purification by silica gel chromatography to afford 3-butenyl 5-aminolevulinate hydrochloride at a yield of 77%.

$^1$H NMR (300 MHz, DMSO-d$_6$): δ8.24 (s, 3H), 5.80~5.74 (m, 1H), 5.16~5.04 (m, 2H), 4.06 (t, J=6.63 Hz, 2H), 2.80 (t, J=6.63 Hz, 2H), 2.52 (t, J=6.6 Hz, 2H), 2.33 (q, J=6.54, 2H); $^{13}$C NMR (75 MHz, DMSO-d$_6$): δ 172.07, 152.64, 143.20, 134.43, 117.07, 62.88, 32.52, 31.90, 28.91

Example 3

Preparation of 4-pentenyl 5-aminolevulinate hydrochloride

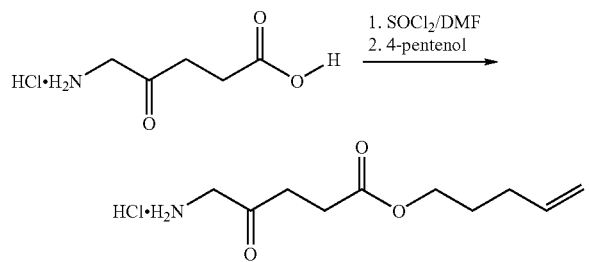

To 1 ml of thionyl chloride (SOCl$_2$) were added 3 drops of N,N-dimethylformamide (DMF) with stirring. Following the addition of 5-aminolevulinic acid hydrochloride (ALA.HCl, 200 mg, 1.19 mmol), the solution was stirred for 12 hours at room temperature. Concentration in a vacuum was conducted before the addition of 4-pentenol. Then, the reaction mixture was stirred for 1.5 hours at room temperature, followed by purification by silica gel chromatography to afford 4-pentenyl 5-aminolevulinate hydrochloride at a yield of 47%.

$^1$H NMR (300 MHz, DMSO-d$_6$): δ8.27 (s, 3H), 5.84~5.73 (m, 1H), 5.06~4.94 (m, 2H), 4.0 (t, J=6.6 Hz, 2H), 3.97 (s, 2H), 2.79 (t, J=6.3 Hz, 2H), 2.54 (t, J=6.6 Hz, 2H), 2.06 (q, J=7.6 Hz, 2H), 1.65 (quintet, J=6.6 Hz, 2H); $^{13}$C NMR (75 MHz, DMSO-d$_6$): δ172.09, 152.67, 143.18, 137.68, 115.20, 63.20, 31.91, 29.39, 28.91, 27.18.

Example 4

Preparation of 5-hexenyl 5-aminolevulinate hydro chloride

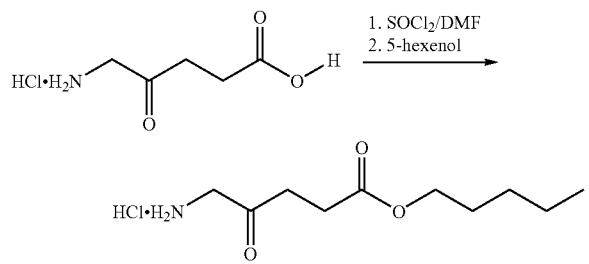

To 1 ml of thionyl chloride (SOCl$_2$) were added 3 drops of N,N-dimethylformamide (DMF) with stirring. Following the addition of 5-aminolevulinic acid hydrochloride (ALA.HCl, 200 mg, 1.19 mmol), the solution was stirred for 12 hours at room temperature. Concentration in a vacuum was conducted before the addition of 5-hexenol. Then, the reaction mixture was stirred for 1.5 hours at room temperature, followed by purification by silica gel chromatography to afford 5-hexenyl 5-aminolevulinate hydrochloride at a yield of 89%.

$^1$H NMR (300 MHz, DMSO-d$_6$): δ8.33 (s, 3H), 5.85~5.71 (m, 1H), 5.04~4.92 (m, 2H), 3.99 (t, J=6.5 Hz, 2H), 3.93 (s, 2H), 2.78 (t, J=6.6 Hz, 2H), 2.53 (t, J=6.6 Hz, 2H), 2.02 (q, J=7 Hz, 2H), 1.56 (quintet, J=6.7 Hz, 2H), 1.38 (quintet, J=5.1 Hz, 2H); $^{13}$C NMR (75 MHz, DMSO-d$_6$): δ 202.66, 172.05, 138.41, 115.02, 63.92, 46.52, 34.26, 32.69, 27.56, 27.08, 24.55.

Example 5

Preparation of cis-2-pentenyl 5-aminolevulinate hydrochloride

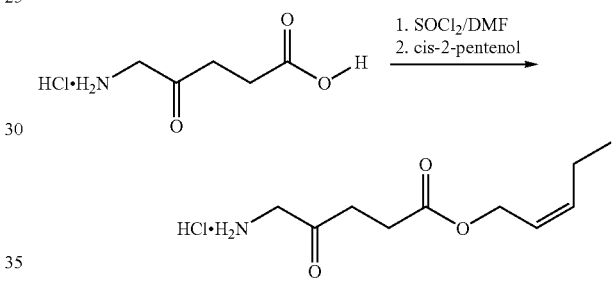

To 1 ml of thionyl chloride (SOCl$_2$) were added 3 drops of N,N-dimethylformamide (DMF) with stirring. Following the addition of 5-aminolevulinic acid hydrochloride (ALA.HCl, 200 mg, 1.19 mol), the solution was stirred for 12 hours at room temperature. Concentration in a vacuum was conducted before the addition of cis-2-pentenol. Then, the reaction mixture was stirred for 1.5 hours at room temperature, followed by purification by silica gel chromatography to afford cis-2-pentenyl 5-aminolevulinate hydrochloride at a yield of 68%.

$^1$H NMR (300 MHz, DMSO-d$_6$): δ8.37 (s, 3H), 5.62~5.58 (m, 1H), 5.47~5.41 (m, 1H), 4.56 (d, J=6.8 Hz, 2H), 3.93 (s, 2H), 2.79 (t, J=6.3 Hz, 2H), 2.53 (t, J=6.5 Hz, 2H), 2.06 (quintet, J=7 Hz, 2H), 0.92 (t, J=7.5 Hz, 3H); $^{13}$C NMR (75 MHz, DMSO-d$_6$): δ171.94, 152.62, 143.18, 136.30, 123.03, 59.60, 31.90, 28.91, 20.27, 13.86

Example 6

Preparation of cis-3-hexenyl 5-aminolevulinic acid hydrochloride

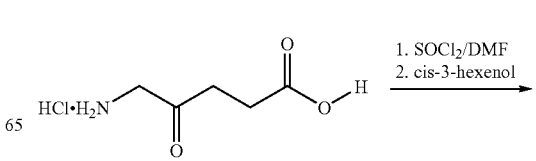

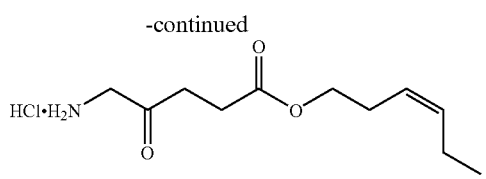

To 1 ml of thionyl chloride (SOCl$_2$) were added 3 drops of N,N-dimethylformamide (DMF) with stirring. Following the addition of 5-aminolevulinic acid hydrochloride (ALA.HCl, 200 mg, 1.19 mmol), the solution was stirred for 12 hours at room temperature. Concentration in a vacuum was conducted before the addition of cis-3-hexenol. Then, the reaction mixture was stirred for 1.5 hours at room temperature, followed by purification by silica gel chromatography to afford cis-3-hexenyl 5-aminolevulinic acid hydrochloride at a yield of 47%.

$^1$H NMR (300 MHz, DMSO-d$_6$) δ8.42 (br s, 3H), 5.43-5.35 (m, 2H), 3.97 (t, J=6 Hz, 2H), 3.91 (s, 2H), 2.79 (t, J=6 Hz, 2H), 2.50 (t, J=6 Hz, 2H), 2.04 (q, J=7 Hz, 2H), 1.59 (quintet, J=7 Hz, 2H), 1.56 (t, J=7 Hz, 3H); $^{13}$C NMR (75 MHz, CDCl$_3$): δ202.59, 172.81, 134.78, 123.83, 64.65, 48.25, 35.21, 27.72, 26.85, 20.83, 14.45.

Example 7

Preparation of cis-4-hexenyl 5-aminolevulinate hydrochloride

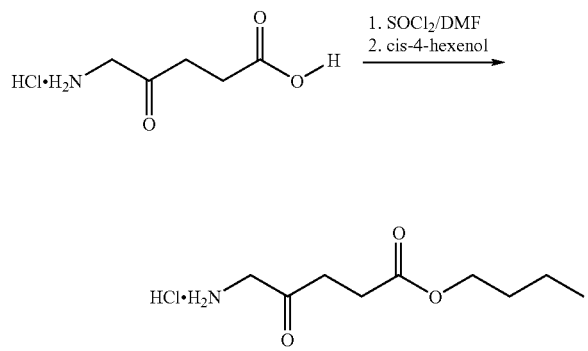

To 1 ml of thionyl chloride (SOCl$_2$) were added 3 drops of N,N-dimethylformamide (DMF) with stirring. Following the addition of 5-aminolevulinic acid hydrochloride (ALA.HCl, 200 mg, 1.19 mmol), the solution was stirred for 12 hours at room temperature. Concentration in a vacuum was conducted before the addition of cis-4-hexenol. Then, the reaction mixture was stirred for 1.5 hours at room temperature, followed by purification by silica gel chromatography to afford cis-4-hexenyl 5-aminolevulinate hydrochloride at a yield of 47%.

$^1$H NMR (300 MHz, CDCl$_3$): δ8.25 (s, 3H), 5.51~5.45 (m, 1H), 5.39~5.33 (m, 1H), 4.28 (s, 2H), 4.05 (t, J=6.7 Hz, 2H), 2.92 (t, J=6 Hz, 2H), 2.65 (t, J=6 Hz, 2H), 2.10 (q, J=7.2 Hz, 2H), 1.67 (t, J=7 Hz, 2H), 1.80 (d, J=6 Hz, 3H); $^{13}$C NMR (75 MHz, DMSO-d$_6$): δ202.35, 172.60, 129.05, 124.92, 64.49, 47.91, 34.96, 28.32, 27.49, 23.12, 12.73.

Example 8

Preparation of trans-2-hexenyl 5-aminolevulinate hydrochloride

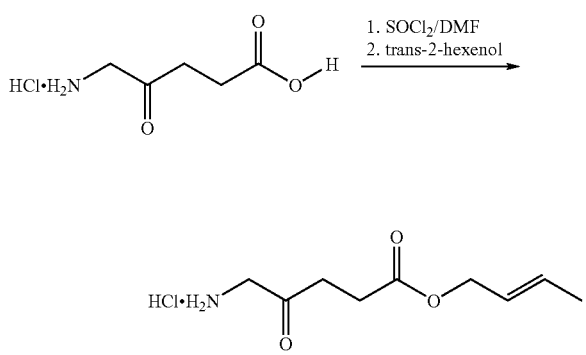

To 1 ml of thionyl chloride (SOCl$_2$) were added 3 drops of N,N-dimethylformamide (DMF) with stirring. Following the addition of 5-aminolevulinic acid hydrochloride (ALA.HCl, 200 mg, 1.19 mmol), the solution was stirred for 12 hours at room temperature. Concentration in a vacuum was conducted before the addition of trans-2-hexenol. Then, the reaction mixture was stirred for 1.5 hours at room temperature, followed by purification by silica gel chromatography to afford trans-2-hexenyl 5-aminolevulinic acid hydrochloride at a yield of 47%.

$^1$H NMR (300 MHz, CDCl$_3$): δ8.21 (s, 3H), 5.81~5.71 (m, 1H), 5.58~5.49 (m, 1H), 4.50 (d, J=6.5 Hz, 2H), 4.27 (s, 2H), 2.92 (t, J=6.5 Hz, 2H), 2.66 (t, J=6.5 Hz, 2H), 2.02 (q, J=7.5 Hz, 2H), 1.40 (sixtet, J=7.4 Hz, 2H), 0.9 (t, J=7.4 Hz, 3H); $^{13}$C NMR (75 MHz, DMSO-d$_6$): δ171.84, 152.62, 143.19, 135.13, 124.19, 64.37, 33.58, 31.88, 28.91, 21.50, 13.41.

Experimental Example

1. Materials

A. Cell Lines

Human epidermal keratinocyte (HEK),

Human dermal fibroblast (hF), squamous cell carcinoma: A431 (KCLB No. 80005)

Malignant melanoma: TXM 13(KCLB No. 80029)

B. Animals

ICR mice (Dae Han Biolink Co. Ltd., Korean Institute of Bioscience and Biotechnology, Korea) 7~8 weeks old, female (♀)

C. Radiation Emitter

An LED (light radiation emitter) was employed as a light source radiating blue light in the wavelength of 410 nm (wavelength band 400-430 nm) and red light (Luxeon, Lumileds Light) in the wavelength of 635 nm (wavelength band 615-645 nm) at a dose of 5-30 J/cm$^2$.

2. Solubility Test

The ALA ester (powder) prepared in Examples were tested for solubility.

The results are summarized in Table 1, below.

TABLE 1

| | Cpds | DMSO | DMF | Ether | EA | MeOH | EtOH | i-PrOH | CHCl$_2$ | H$_2$O |
|---|---|---|---|---|---|---|---|---|---|---|
| ALA | 5-Aminolevulinic acid | ○ | ○ | X | X | ○ | ○ | X | X | ○ |
| ALA-1 | 5-Aminolevulinic acid methyl ester | ○ | ○ | X | X | ○ | ○ | ○ | X | ○ |
| ALA-2 | 5-Aminolevulinic acid allyl ester | ○ | ○ | X | X | ○ | ○ | ○ | ○ | ○ |
| ALA-3 | 5-Aminolevulinic acid 3-butenyl ester | ○ | ○ | X | Δ | ○ | ○ | ○ | ○ | ○ |
| ALA-4 | 5-Aminolevulinic acid 4-pentenyl ester | ○ | | | | ○ | ○ | | ○ | ○ |
| ALA-5 | 5-Aminolevulinic acid cis-2-pentenyl ester | ○ | | | | ○ | ○ | | ○ | ○ |
| ALA-6 | 5-Aminolevulinic acid 5-hexenyl ester | ○ | ○ | X | Δ | ○ | ○ | ○ | ○ | ○ |

○ high solubility, Δ medium solubility X low solubility

As seen in Table 1, the ALA esters of the present invention are highly soluble in alcohol, water, and DMSO.

Thus, the ALA esters of the present invention may employ either of any aqueous and oily vehicles for the formulation of topical ointments.

3. Cytotoxicity Test (Cell Survival Test)

Cytotoxicity was conducted through an MTT assay (Chemicon, Serologicals Corporation, USA) as follows.

Cells were seeded at a density of $3 \times 10^4$ cells/well in 96-well plates (Nunc Do, Denmark).

When the cells were at a confluence of about 60~70%, 24 hours after seeding, the media was exchanged for 100 μl of fresh, serum-free media containing various respective concentrations of ALA or ALA-ester, after which the cells were incubated for an additional 24 hours.

An MTT solution (0.5 mg/mL) was added in an amount of 10 μl to each well, followed by incubation for 4 hours to form formazan crystals. A color-developing solution (isopropanol with 0.04 N HCl) was added in an amount of 100 μl per well to solubilize the formazan crystals.

The plates were measured for absorbance at 570 nm using an ELISA reader (EMAX, Molecular Device, USA).

(1) Human Epidermal Keratinocyte (HEK)

Cell survival of the human epidermal keratinocytes treated with ALA esters of the present invention and with ALA was compared. The results are summarized in Tables 1 and 2, which are represented in different manners depending on the measurements.

TABLE 2

| | ALA(OD) | ALA-1 | ALA-3 | ALA-4 | ALA-6 |
|---|---|---|---|---|---|
| C | 3.513 | 3.327 | 3.47 | 3.625 | 3.429 |
| 0.01 mM | 3.428(97.6%) | 2.952(88.8%) | 2.919(83.8%) | 2.8(77.3%) | 3.13(91.2%) |
| 0.05 mM | 3.318(94.5%) | 3.482(104.5%) | 3.57(102.8%) | 2.603(71.6%) | 3.413(99.4%) |
| 0.1 mM | 3.457(98.5%) | 3.313(99.6%) | 3.413(98.2%) | 2.98(82%) | 3.18(92.7%) |
| 0.5 mM | 3.285(92.8%) | 3.421(102.7%) | 2.838(81.8%) | 2.561(70.5%) | 2.521(73.4%) |
| 1 mM | 2.802(79.7%) | 3.435(103%) | 2.592(74.9%) | 2.475(68.3%) | 2.548(74.3%) |
| 2 mM | 2.179(62.1%) | 3.093(93%) | 2.185(63.1%) | 2.407(66.3%) | 2.306(67.3%) |
| 5 mM | 1.659(47.2%) | 2.398(69%) | 2.101(60.5%) | 1.354(37.1%) | 1.388(40.2%) |

ALA-1; ALA methylester, ALA-3: ALA butenylester, ALA-4: ALA pentenylester, ALA-6: ALA hexenylester

TABLE 3

| Conc. (mM) | ALA Avg (%) ± SD (%) | ALA-1 Avg (%) ± SD (%) | ALA-3 Avg (%) ± SD (%) | ALA-4 Avg (%) ± SD (%) | ALA-6 Avg (%) ± SD (%) |
|---|---|---|---|---|---|
| C | 100 ± 6.92 | 100 ± 4.56 | 100 ± 10.25 | 100 ± 7.68 | 100 ± 1.25 |
| 0.01 | 131.83 ± 0.9 | 116.69 ± 1 | 116.69 ± 0.69 | 81.43 ±± 0.69 | 106.44 ± 0.37 |
| 0.05 | 112.32 ± 0.7 | 94.01 ± 0.71 | 94.01 ± 0.59 | 66.21 ± 0.59 | 77.97 ± 0.88 |
| 0.1 | 132.21 ± 0.35 | 125.58 ± 1.05 | 125.58 ± 0.51 | 53.63 ± 0.51 | 69 ± 3.42 |
| 0.5 | 103.43 ± 0.15 | 88.14 ± 0.95 | 88.14 ± 0.51 | 50.17 ± 0.51 | 61.39 ± 3.22 |
| 1 | 100.94 ± 6.16 | 72.02 ± 3.52 | 72.02 ± 3.82 | 57.17 ± 1.60 | 62 ± 5.58 |
| 2 | 84.9 ± 5.12 | 83.69 ± 1.54 | 83.69 ± 4.75 | 44.82 ± 3.43 | 62 ± 1.59 |

(2) Human Dermal Fibroblast (hF)

TABLE 4

| Conc. (mM) | ALA Avg (%) ± SD (%) | ALA-1 Avg (%) ± SD (%) | ALA-3 Avg (%) ± SD (%) | ALA-4 Avg (%) ± SD (%) | ALA-6 Avg (%) ± SD (%) |
|---|---|---|---|---|---|
| C | 103.3 ± 16.38 | 100.34 ± 6.5 | 100.86 ± 14.66 | 100.09 ± 7.31 | 100.57 ± 7.22 |
| 0.01 | 109.74 ± 11.55 | 110.33 ± 15.01 | 114.28 ± 5.4 | 101.13 ± 13.45 | 113.29 ± 13.51 |
| 0.05 | 125.18 ± 14.08 | 116.86 ± 17.63 | 126.76 ± 3.88 | 114.49 ± 17.1 | 98.47 ± 13.03 |
| 0.1 | 125.27 ± 16.1 | 110.44 ± 17.98 | 115.65 ± 6.85 | 103.35 ± 14.09 | 92.42 ± 13.86 |
| 0.5 | 95.218 ± 9.47 | 113 ± 22.58 | 110.21 ± 4.21 | 95.81 ± 10.6 | 91.41 ± 9.04 |
| 1 | 99.89 ± 18.3 | 120.48 ± 10.91 | 96.59 ± 16.88 | 100.32 ± 6.36 | 80.78 ± 5.6 |
| 2 | 97.66 ± 9.45 | 87.65 ± 14.77 | 94.97 ± 9.7 | 93.13 ± 8.07 | 86.12 ± 5.37 |

(3) Squamous Cell Carcinoma (A431)

TABLE 5

| Conc. (mM) | ALA Avg (%) ± SD (%) | ALA-1 Avg (%) ± SD (%) | ALA-3 Avg (%) ± SD (%) | ALA-4 Avg (%) ± SD (%) | ALA-6 Avg (%) ± SD (%) |
|---|---|---|---|---|---|
| C | 101.04 ± 0.92 | 100 ± 1.00 | 101.41 ± 0.69 | 100.58 ± 0.72 | 100.79 ± 0.79 |
| 0.01 | 102.99 ± 0.71 | 101.03 ± 0.71 | 104.08 ± 0.59 | 101.68 ± 0.81 | 101.04 ± 0.88 |
| 0.05 | 104.98 ± 0.35 | 103.06 ± 1.05 | 105.59 ± 0.51 | 102.51 ± 0.54 | 91.32 ± 3.42 |
| 0.1 | 106.79 ± 0.15 | 105. 64 ± 0.95 | 105.48 ± 0.51 | 93.24 ± 2.17 | 86.8 ± 3.22 |
| 0.5 | 81.6 ± 6.16 | 101.75 ± 3.52 | 97.46 ± 3.82 | 80.91 ± 1.6 | 84.16 ± 5.58 |
| 1 | 84.17 ± 5.12 | 101.45 ± 1.54 | 97.65 ± 4.75 | 80.11 ± 3.43 | 88.47 ± 4.59 |
| 2 | 82.63 ± 2.44 | 98.4 ± 1.2 | 102.85 ± 1.53 | 84.57 ± 1.77 | 66.21 ± 4.43 |

(4) Malignant Melanoma (TMX 13)

TABLE 6

| Conc. (mM) | ALA Avg ± SD (%) | ALA-1 Avg ± SD (%) | ALA-3 Avg ± SD (%) | ALA-4 Avg ± SD (%) | ALA-6 Avg ± SD (%) |
|---|---|---|---|---|---|
| C | 99.06 ± 6.92 | 101.15 ± 3.56 | 100.28 ± 8.91 | 100.17 ± 10.33 | 99.99 ± 10.88 |
| 0.01 | 100 ± 10.22 | 104.69 ± 6.64 | 102.16 ± 10.55 | 96.3 ± 14.69 | 92.05 ± 9.09 |
| 0.05 | 93.12 ± 5.82 | 100.34 ± 4.39 | 95.03 ± 10 | 83.42 ± 12.09 | 99.41 ± 8.25 |
| 0.1 | 86.66 ± 6.95 | 87.37 ± 8.13 | 96.89 ± 7.99 | 72.55 ± 9.25 | 81.45 ± 6.38 |
| 0.5 | 83.75 ± 9.57 | 64.59 ± 3.95 | 90.58 ± 3.8 | 75.01 ± 13.79 | 77.18 ± 8.17 |
| 1 | 89.91 ± 6.33 | 69.86 ± 8.83 | 92.34 ± 4.31 | 60.95 ± 8.31 | 76.06 ± 6.81 |
| 2 | 93.6 ± 5.13 | 69.94 ± 13.42 | 78.81 ± 6.22 | 49.85 ± 53.24 | 53.24 ± 6.8 |

As described in Tables 1 to 5, all of the cells except for HEK were observed to have a cell survival of 70% or higher when treated with ALA and ALA esters, which indicates that the unsaturated alkyl esters of ALA according to the present invention are not cytotoxic compared to ALA.

4. Fluorescence Spectroscopy

The synthesis of PpIX, induced by ALA and unsaturated alkyl esters of ALA in cells and skin tissues, was quantified using fluorescence spectroscopy.

The intensity of PpIX was measured on a fluorescence spectrophotometer (Uvikon, model 943) with excitation at 408 nm.

A. Cell Line

Each cell line was plated at a density of $2 \times 10^5$ cells in a 10 cm²-dish (Falcon), and when the cells reached a confluent state of 70~80%, serum-free media containing various concentrations (0.001~1 mM) of ALA or ALA esters was added to the cells, followed by incubation for 4 hours.

After being washed once with PBS, the cells were detached with a 50% methanol solution containing 1M hypochlorite ($HClO_4$) and scraped off using a Costar cell scraper.

The cells thus harvested were incubated for 5 min and centrifuged.

The fluorescence of the supernatant thus obtained was determined using a spectrofluorometer with excitation at 405 nm and emission at 605 nm.

Figure 2:
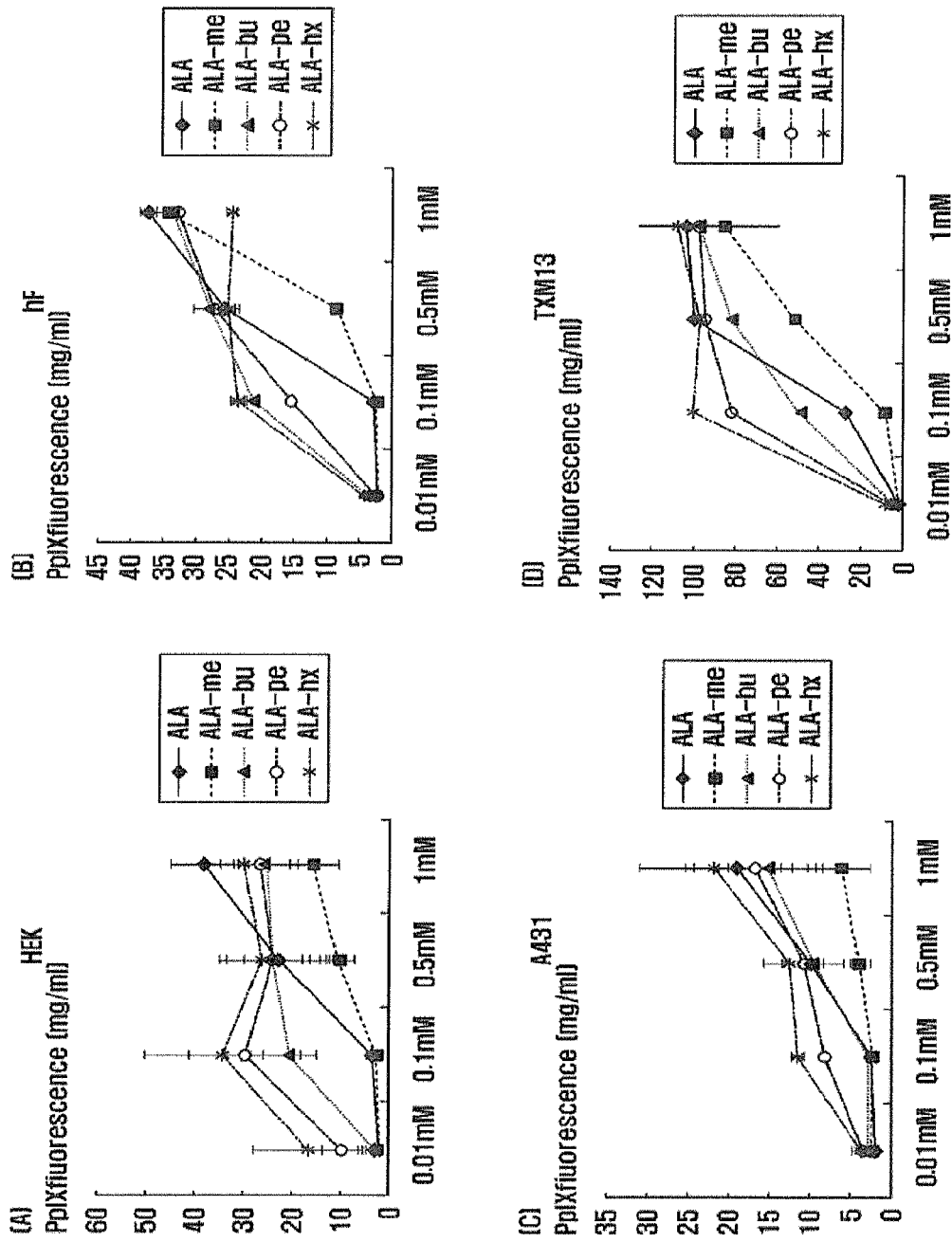
FIG. 2 shows the amounts of PpIX synthesized in various cell lines treated with ALA esters of the present invention in graphs.

The results are graphed in FIGS. 1 and 2.

As seen in FIG. 1, the ALA esters of the present invention, that is, ALA-1, 4 and 6, induced greater PpIX synthesis in A431 cells than did ALA Also, PpIX synthesis was observed to increase in a dose-dependent manner over the range from 0.01 to 1 mM of both ALA and ALA esters in all cell lines. Further, when compared in the same cell line, the ALA esters of the present invention, that is, unsaturated alkyl esters of 5-aminolevulinic acid, induced the intracellular synthesis of PpIX more efficiently than did ALA (FIG. 2). In FIG. 2, human epithelium keratocyte (HEK) is assigned to (A), human dermal fibroblast (hF) to (B), squamous cell carcinoma (A431) to (C), and malignant melanoma (TXM13) to (D).

As explained above, the ALA esters of the present invention can induce PpIX so as to be synthesized in both normal cells and cancer cells.

B. Organ (1) Preparation of Ointment

ALA or the ALA esters of the present invention were admixed with a water-soluble base (SamA Base, Korea) containing stearyl alcohol, polyethylene glycol and pure water to afford ointments comprising ALA or ALA esters in amounts of 5%, 10% and 15% (w/w).

(2) Clinic

The ointments prepared above were applied in a predetermined amount (25 g) to the back of shaved ICR mice.

1 or 4 hours after the application, the ICR mice were sacrificed by dislocating the cervix thereof, and the skin was sampled therefrom.

500 mg of each skin sample was placed in 2 ml of trypsin/EDTA and homogenized at 30,000 rpm for 5 min using a tissue homogenizer.

The homogenates were trypsinized at 37° C. for 1 hour in a darkroom, added with 2 ml of 50% (w/w) methanol containing 1M perchloric acid, and centrifuged.

The supernatant thus obtained was measured for fluorescence on a spectrofluorometer with excitation at 405 nm and emission at 605 nm.

Figure 3:
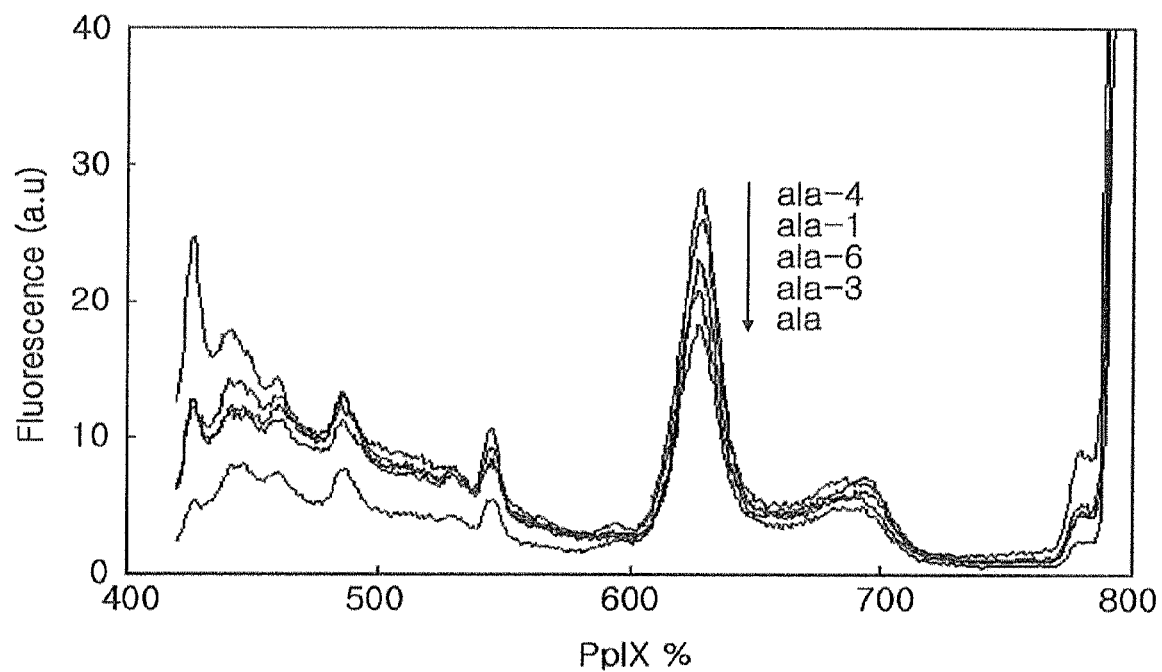
FIG. 3 is a graph showing the amounts of PpIX synthesized in the skin treated with the ALA ester of the present invention in comparison with that of ALA.
Figure 4:
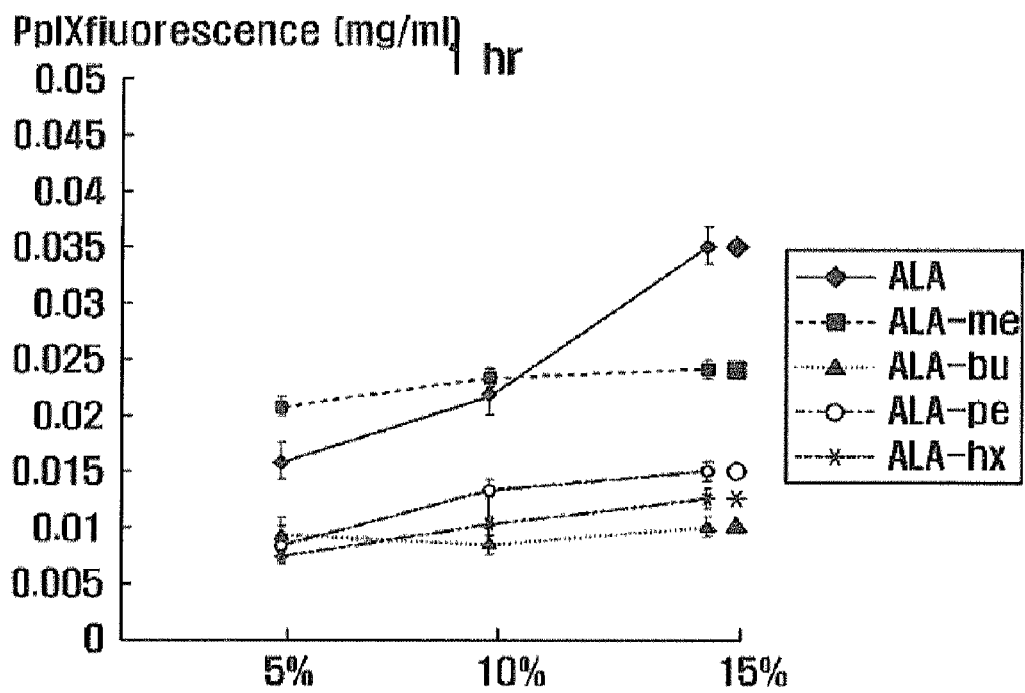
FIG. 4 shows the amounts of PpIX synthesized in the skin 1 hour (A) and 4 hours (b) after treatment of the skin with the ALA ester of the present invention in a dose dependent manner.
Figure 4:
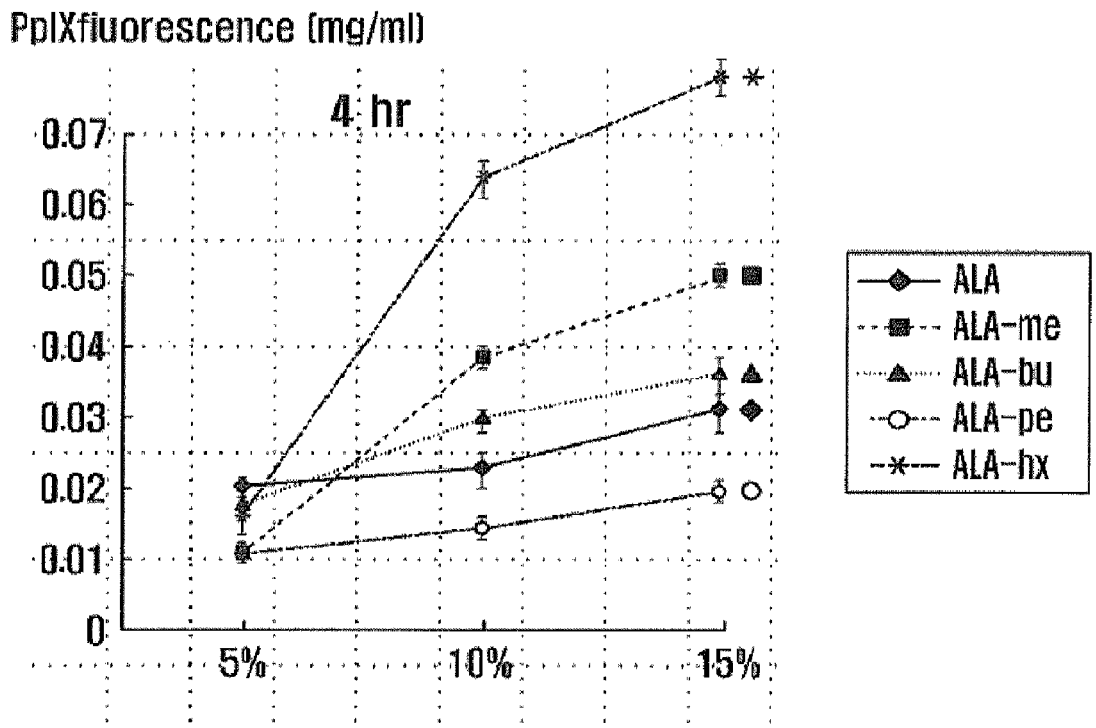

The results are shown in FIGS. 3 and 4.

Like ALA, as seen in the fluorescence spectra of FIG. 3, ALA esters of the present invention can be absorbed into cells to synthesize PpIX. Furthermore, the ALA esters of the present invention can pass through cell membranes more easily, to thus induce the synthesis of a greater amount of the photosensitizer PpIX than can ALA.

It was also observed that the ALA esters of the present invention were superior to ALA in ability to synthesize the photosynthesizer PpIX as a result of more efficient penetration into the bilayer of the stratum corneum. In addition, PpIX synthesis in the skin cells depends on the duration time and amount of ointment applied to the skin (FIG. 4).

5. Observation Under Fluorescence Microscope

Each cell line and ICR mouse skin tissue were treated with the ALA esters of the present invention, and the regions where PpxIX was expressed were observed under a fluorescence microscope.

A. Cell Line

The normal cell lines, human epidermal keratinocytes (HEK) and human dermal fibroblasts (hF) and the cancer cell lines squamous cell carcinoma A431 and malignant melanoma TXM13 were treated with **mM of the ALA esters of the present invention or ALA, followed by monitoring the fluorescence of the synthesized PpIX under a fluorescence microscope.

Figure 5:
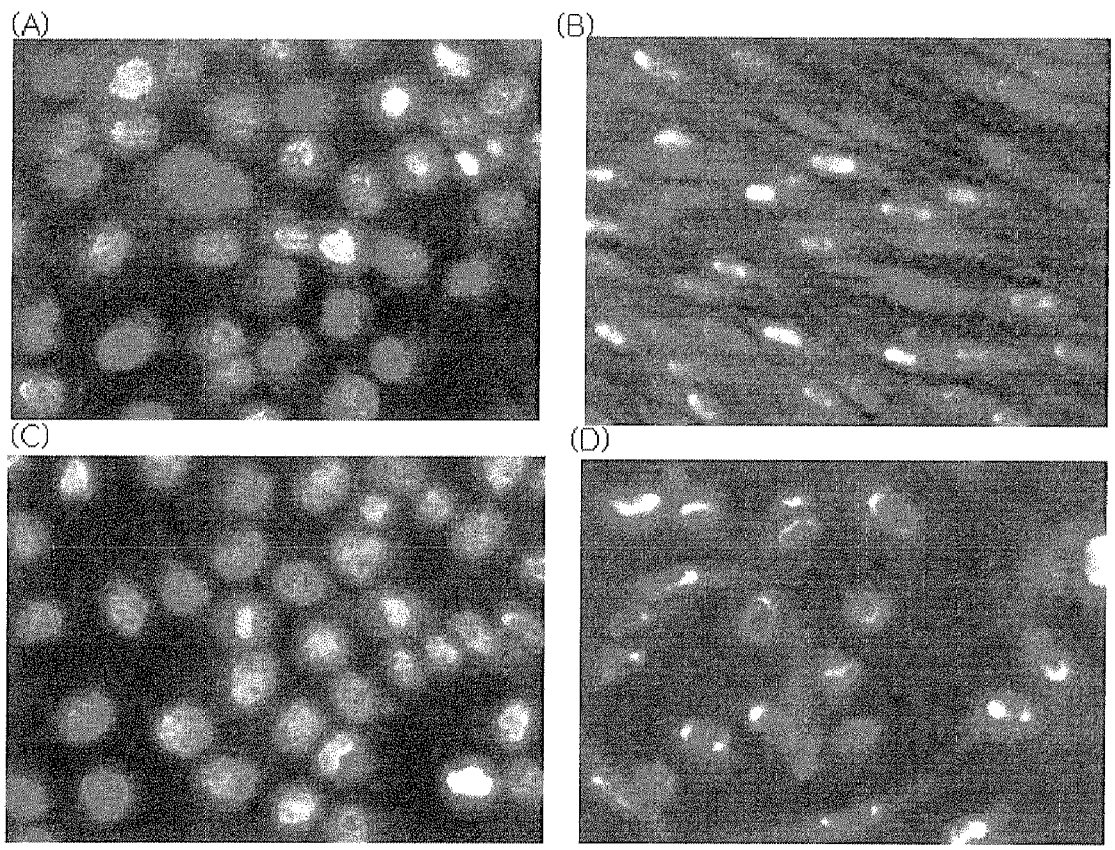
FIG. 5 shows the fluorescence of PpIX synthesized in the cytoplasms of the healthy cells treated with the ALA esters of the present invention.

As seen in FIG. 5, human epidermal keratinocyte (HEK), human dermal fibroblast (hF), squamous cell carcinoma (A431), and malignant melanoma (TXM 13) were all observed to accumulate PpIX in their respective cytoplasms, indicating that ALA esters of the present invention as well as ALA can induce the synthesis of PpIX in both normal and cancer cell lines.

B. Dermal Tissue

Ointments comprising the ALA esters of the present invention or ALA were applied to the skin of ICR mice, followed by monitoring the synthesis of PpIX under a fluorescence microscope with time, e.g., 1, 2 and 3 hours after the application.

The results are shown in FIGS. 6 and 7.

As apparent in FIG. 6, the amount of the PpIX synthesized was observed to increase with the lapse of time after the application in the normal skin tissues of ICR mice. Intense PpIX synthesis was found particularly in the epidermis and the sebaceous gland with the lapse of time. In FIG. 6, the results, obtained 1 hour after the is application, are assigned to (A), 2 hours to (B), 3 hours to (C) and the application of ALA to control.

Also, as seen in FIG. 7, PpIX was expressed specifically in cancer lesions.

Taken together, the data obtained above indicate that the ointments comprising the ALA esters of the present invention are useful in the treatment of specific legions.

6. Research into Apoptosis and Cell Death

A. Cell Line

Each cell line cultured in 6-well plates was treated with ALA or ALA esters of the present invention, irradiated with visible light from an LED, and stained with Annexin V-FITC and PI (Annexin V-FITC Apoptosis detection Kit, BD) before the measurement of apoptosis using flow cytometry (FACS-Calibur, BD, USA).

The results are graphed in FIG. 8.

As seen in FIG. 8, cells showed 85% or higher cell survival when they were treated with neither ALA nor unsaturated alkyl esters of ALA of the present invention, treated with ALA or unsaturated alkyl esters of ALA, but with no irradiation with visible light, or just irradiated with visible light (5-20 $J/cm^2$) (FIGS. 8A and B). In contrast, irradiation (5-20 $J/cm^2$) subsequent to treatment with 1 mM ALA or ALA esters of the present invention induced the cells to undergo apoptosis (Annexin V+/PI–) or the late stage of apoptosis (Annexin V+/PI+) (FIGS. 8C and D).

B. Skin Tissue

Ointments comprising ALA or the ALA esters of the present invention at various concentrations (5~15%) were applied in a predetermined amount (25 g) to the back of shaved ICR mice.

1 and 4 hours after the application, the back was irradiated with LED visible light (dose 25 $J/cm^2$).

24, 48 and 72 hours after the irradiation, skin samples were taken from the back of the mice, stained with hematoxylin-eosin (H&E) and observed for cell death.

The results are shown in FIGS. 8 and 10.

As seen in FIG. 9, the mice which were irradiated with visible light subsequent to the application of ALA or the ALA esters of the present invention underwent apoptosis or necrosis of the epidermis 24 hours after irradiation (FIG. 9A) and underwent both necrosis and rejuvenation 48 hours after irradiation (FIGS. 9B and 9C). In FIG. 9, (A) shows the skin tissue 24 hours after the irradiation of visible light in a dose of 25 $J/cm^2$ subsequent to the application of ALA thereto, (B) the skin tissue 48 hours after the irradiation of visible light in a dose of 25 25 $J/cm^2$ subsequent to the application of ALA-1 (ALA-methyl ester) thereto, (C) the skin tissue 48 hours after the irradiation of visible light in a dose of 25 $J/cm^2$ subsequent to the application of ALA-6 (ALA-hexenyl ester) thereto, and (D) the skin tissue after the application of unsaturated alkyl ester thereto, with no irradiation.

As seen in FIG. 10, the sebaceous gland was destroyed partially or wholly, indicating that the compounds of the present invention are effective in the treatment of acne. In FIG. 10, (A) shows the skin tissue 24 hours after the irradiation of visible light in a dose of 25 $J/cm^2$ subsequent to the application of ALA thereto, (B) the skin tissue 24 hours after the irradiation of visible light in a dose of 25 $J/cm^2$ subsequent to the application of ALA-1 (ALA-methyl ester) thereto, (C) the skin tissue 24 hours after the irradiation of visible light in a dose of 25 $J/cm^2$ subsequent to the application of ALA-6 (ALA-hexenyl ester) thereto, and (D) the skin tissue after the application of unsaturated alkyl ester thereto, with no irradiation.

7. Patch Test

In order to examine whether the ointment prepared in Example 4-(B)-(1) is causative of allergic and primary contact dermatitis, a patch test was performed on 50 normal persons.

Ointments having 5%, 10% and 15% (w/w) of the compound of interest were applied to the skin of 60 normal ICR mice and removed therefrom with distilled water 6 and 12 hours after application. These mice were monitored for skin condition with the naked eyes for 90 days, in comparison with a control group of 20 which was treated with no ointments.

The skin of normal bodies was coated with 5%, 10% and 15% ointments and sealed for 6, 12 and 24 hours before examination.

Mice (not shown) and the human skin (FIG. 11) were all observed to be negative.

Therefore, the ointment comprising the ALA esters of the present invention was found to cause neither allergic nor primary contact (phototoxic) dermatitis.

8. Therapeutic Effect of the Ointment on Skin Diseases

Patients suffering from acne, actinic keratosis, arsenical keratosis or basal cell cancer were treated with photodynamic therapy using an ointment comprising 15% (w/w) of ALA-6 (ALA hexenyl ester).

As is apparent from FIGS. 12 to 19, the ointment according to the present invention is very useful in the treatment of acne, actinic keratosis, arsenical keratosis and basal cell cancer. Therapeutic effects on acne are shown in FIGS. 12 to 17, therapeutic effects on actinic keratosis in FIG. 18A, therapeutic effects on arsenical keratosis in FIG. 18B, and therapeutic effects on basal cell cancer in FIG. 19.

[Industrial Applicability]

As described hitherto, the present invention provides non-toxic, unsaturated alkyl esters of ALA which can be used in photodynamic therapy for skin diseases with more effective therapeutic efficacy than conventional ALA. Also, a method for preparing the therapeutically effective compounds is provided. A pharmaceutical composition comprising the compound of the present invention as an active ingredient is also within the scope of the present invention.

The invention claimed is:

1. An unsaturated alkyl ester of 5-aminolevulinic acid, represented by the following chemical formula I, or a pharmaceutically acceptable salt thereof:

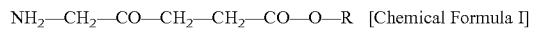

wherein, R is selected from the group consisting of 2-propenyl, 3-butenyl, 4-pentenyl, 5-hexenyl, cis-2-pentenyl, cis-3-hexenyl, cis-4-hexenyl, and trans-2-hexenyl.

2. The unsaturated alkyl ester of 5-aminolevulinic acid or the pharmaceutically acceptable salt thereof according to claim 1, wherein the pharmaceutically acceptable salt is a hydrochloride.

3. A method for preparing the unsaturated alkyl ester of 5-aminolevulinic acid of claim 1, comprising:
   (a) reacting a compound, represented by the following chemical formula II, with thionyl chloride and N,N-dimethylformamide; and
   (b) reacting a product of step (a) with an unsaturated alcohol selected from the group consisting of allyl alcohol, 3-butenol, 4-pentenol, 5-hexenol, cis-2-pentenol, cis-3-hexenol, cis-4-hexenol and trans-2-hexenol:

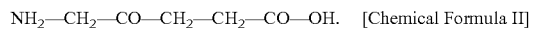

4. A pharmaceutical composition for the treatment of a skin disease, comprising the unsaturated alkyl ester of 5-aminolevulinic acid of claim 1 or the pharmaceutically acceptable salt thereof as an active ingredient.

5. The pharmaceutical composition according to claim 4, wherein the skin disease is acne or skin cancer.

* * * * *